United States Patent [19]

Butland

[11] Patent Number: 5,360,628
[45] Date of Patent: Nov. 1, 1994

[54] TECHNIQUE FOR LABELING AN OBJECT FOR ITS IDENTIFICATION AND/OR VERIFICATION

[75] Inventor: Charles L. Butland, Playa del Rey, Calif.

[73] Assignee: Butland Trust Organization, Los Angeles, Calif.

[21] Appl. No.: 8,620

[22] Filed: Jan. 22, 1993

Related U.S. Application Data

[63] Continuation-in-part of Ser. No. 597,859, Oct. 15, 1990, Pat. No. 5,194,289, which is a continuation-in-part of Ser. No. 263,058, Oct. 27, 1988, abandoned, which is a continuation-in-part of Ser. No. 868,955, May 30, 1986, Pat. No. 4,882,195, which is a continuation-in-part of Ser. No. 857,929, Apr. 30, 1986, abandoned.

[51] Int. Cl.$^5$ .............................................. B44F 1/12
[52] U.S. Cl. .......................................... 427/7; 427/60; 427/261; 427/384; 427/385.5; 427/407.1; 427/417
[58] Field of Search ................ 427/7, 60, 261, 384, 427/385.5, 407.1, 417

[56] References Cited

U.S. PATENT DOCUMENTS

| | | | |
|---|---|---|---|
| 3,886,083 | 5/1975 | Laxer | 427/7 |
| 4,360,548 | 11/1982 | Skees et al. | 427/7 |
| 4,540,595 | 10/1985 | Acitelli et al. | 427/7 |
| 4,579,370 | 4/1986 | Corwin et al. | 427/7 |
| 4,662,653 | 5/1987 | Greenaway | 427/7 |
| 4,892,385 | 1/1990 | Webster et al. | 427/7 |

*Primary Examiner*—Janyce Bell
*Attorney, Agent, or Firm*—Mueller and Smith

[57] ABSTRACT

The present invention is addressed to providing a simple, yet reliable method for labeling an object for its verification. Broadly, the method of the present invention for labeling an object for its verification commences with applying to a predetermined location on said object, a mark which creates a permanent impression thereof which is perceptible to the unaided or naked eye and a mark which creates a permanent impression thereof which is imperceptible to the unaided or naked eye, yet which can be determined by mechanical, electrical, and/or biologic means. In prior U.S. Pat. No. 5,194,289 a combination of UV eye and amino acid/protein fragment was used to label objects for their identification. The present invention broadens such dual labeled scheme to include a variety of additional "invisible" labeling techniques. Additionally, the present invention includes the recognition that, in order to stop counterfeiting of records and like consumer goods, a visible mark also must be present on the object. A hologram or other visible indicia would provide the owner (and the copyist) with one level of protection in ascertaining the genuineness of the object. The second means is "invisible" to the owner (and the copyist) and is designed to be difficult (if not impossible) for the copyist to duplicate.

9 Claims, No Drawings

TECHNIQUE FOR LABELING AN OBJECT FOR ITS IDENTIFICATION AND/OR VERIFICATION

CROSS-REFERENCE TO RELATED APPLICATIONS

This application is a continuation-in-part of U.S. application Ser. No. 07/597,859, filed Oct. 15, 1990, now U.S. Pat. No. 5,194,289, which in turn is a continuation-in-part of U.S. application Ser. No. 07/263,058, filed Oct. 27, 1988, now abandoned which in turn is a continuation-in-part of U.S. application Ser. No. 868,955, filed May 30, 1986, now U.S. Pat. No. 4,882,195 which in turn is a continuation-in-part of U.S. application Ser. No. 857,929, filed Apr. 30, 1986, now abandoned, the disclosures of which are expressly incorporated herein by reference.

BACKGROUND OF THE INVENTION

The present invention relates to the labeling of objects for verifying authenticity and more particularly to the use of a selectively-perceptible mark in combination with a perceptible mark for labeling of objects.

Many objects require verification for authenticity. Such objects include paintings, sculptures, cartoon cells, sports and other collectibles, and like works of art; video cassette recorders, televisions, and like household objects; and computers; printers, and like office and business equipment. Other instances of identification in order to verify ownership, include, for example, records, audio and video tape cassettes, computer software recorded on floppy disks or diskettes, perfumes, designer clothes, handbags, briefcases, cartoon cells, automobile/airplane parts, securities (e.g., stock certificates), wills, and like objects. Many American industries have been plagued by a flagrant piracy explosion over the past decade involving many of the foregoing products. Often, these objects have no serial number or other unique means of identification, or the number can be removed easily following a theft. Alternatively, counterfeiting of such objects has become a thriving business and the need to identify authentic from counterfeit objects is of great importance. Thus, a simple method for reliably identifying or authenticating such objects would be welcomed by the owners, the manufacturers of such objects, and even the U.S. Customs Service.

BROAD STATEMENT OF THE INVENTION

The present invention is addressed to providing a simple, yet reliable method for labeling an object for its verification. Broadly, the method of the present invention for labeling an object for its verification and/or identification comprises applying to a predetermined location on said object, a mark which creates a permanent impression thereof which is perceptible to the unaided or naked eye and a mark which creates a permanent impression thereof which is imperceptible to the unaided or naked eye, yet which can be determined by mechanical, electrical, and/or biologic means. In prior U.S. Pat. No. 5,194,289 (cited above), a combination of UV eye and amino acid/protein fragment was used to label objects for their identification. The present invention broadens such dual labeled scheme to include a variety of additional "invisible" labeling techniques. Additionally, the present invention includes the recognition that, in order to stop counterfeiting of records and like consumer goods, a visible mark also must be present on the object. A hologram or other visible indicia would provide the owner (and the copyist) with one level of protection in ascertaining the genuineness of the object. The second means is "invisible" to the owner (and the copyist) and is designed to be difficult (if not impossible) for the copyist to duplicate.

Advantages of the present invention include a simple, yet reliable means for labeling objects for identification. Another advantage is that a portion of the label is not perceptible to people absent the application of special techniques in order to determine the presence of such labels. Another advantage is that the label can last for an almost indefinite period of time. A yet further advantage is the ease and versatility for identification which is afforded by the present invention. These and other advantages will become readily apparent to those skilled in the art based upon the disclosure contained herein.

DETAILED DESCRIPTION OF THE INVENTION

Once an object is identified and verified, it can be labeled in accordance with the inventive technique disclosed herein so that its authentication at a later date is materially enhanced. For present purposes, "permanent" as applied to the present labeling technique on the object means that the label is incapable of being removed from the object in the ordinary course of intended handling and usage of the object for a time adequate for identification and/or verification of the object to occur. For some objects, it may be desirable that the label remain affixed to the object and identifiable for many years. Such objects would include works of art, household and business appliances, machinery, automobiles, automobile parts, records, video audio tape cassettes, computer software diskettes, and the like. It is conceivable that some objects would require verification for only a limited time (e.g., for several days to several months); however, it is believed that extended verification time periods will find greater acceptance in the market place.

The present invention includes the recognition that in order to stop counterfeiting of, for example, consumer goods, a visible mark must be present on the object. A first mark or indicia which is readily perceptible to the naked or (mechanically) unaided eye, then, is applied to the object. Such a mark would include a picture, signature, visible fingerprint, hologram, or other convention identification mark. Holograms have particular appeal because of the limited number of companies that have the ability to create holograms for application to objects as an identification tool. Thus, a level of protection in ascertaining the authenticity of the object is provided by the visible mark.

The second means of identification and/or verification is invisible to the owner (and the copyist). The functions of the combination of visible and invisible marks includes the designed difficulty with which the copyist should be faced in duplicating both marks and the ability to field test the authenticity in many instances by use of invisible light radiation (UV or IR), an electrical probe measuring electrical resistivity, and the like. Such "invisible" marks include, for example, ultraviolet (UV) dyes, infrared radiation dyes, electrical resistivity inks, and biologic markers. UV dyes and their application in identification can be found in U.S. Pat. No. 5,194,289 cited above. IR 140 is 5,5'-dichloro- 11- diphenylamino-3,3'-diethyl- 10, 12-ethylenethiatricarbocyanine perchlorate (CAS53655-17-7) and it will absorb energy and reemit it at a longer wavelength (i.e., far infrared range of the spectrum). Since the reemitance wavelengths can be viewed at a selected nanometer wavelength, use of an infrared converter and "night vision" goggles for intensifying the image, then, enables the viewing of such reflected wavelengths of energy which cannot be perceived by the naked or unaided eye.

Electrically conductive inks which utilize electrically-conductive particles is yet another technique for "invisibly" labeling an object. The visible mark itself could be applied to the object using inks that exhibit a predetermined electrical resistivity. Use of electrically-conductive pigments, e.g., carbon, silver, gold, copper, aluminum, or the like, renders the ink electrically conductive which enables its resistivity to easily measured even in the field. In fact, use of magnetic particles, (e.g., iron oxide) may even produce ink that can be identified by its magnetic properties.

Another technique utilizes biologic markers, such as amino acids and proteins as disclosed in U.S. Pat. No. 5,194,289, cited above. Such biologic materials can be profiled by gas chromatography which creates a standard for later comparison with a small (e.g., nanogram) sample of ink from a "stolen" object labeled in accordance with the precepts of the present invention. Additionally, U.S. Pat. No. 5,139,812 discloses the use of nucleic acid sequences in ink for identifying an object with a probe. U.S. Pat. No. 4,880,750 discloses the use of individual-specific antibodies (e.g., in an ink) for identification of security documents. U.S. Pat. No. 4,441,943 uses synthetic polypeptides for labeling explosives. The disclosures of these citations are expressly incorporate herein by reference. Such techniques also are not readily perceptible without the aid of special equipment and/or chemicals which develop the presence of such markers. For present purposes, such markers are unique and not easily (if at all) replicated by the forger or counterfeiter. The foregoing biologic markers may be incorporated into a visible or an invisible ink for use in labeling objects. It should be understood also that such biologic markers can be native or can be synthetic, including fragments, single chains, and a variety of additional forms currently developed or yet to be developed. It may even be feasible to radiolabel some biologic or other markers and determine their presence thereby.

The present invention can be implemented readily and has versatility in that a variety of techniques can be used to identify and/or verify an object. Several of the identification techniques can be implemented in the field, while others require laboratory equipment and processing. Combining such techniques permits screening in the field with later absolute verification coming from laboratory analysis. Such ease of use and versatility adds to the effectiveness of the present invention as a deterrent to crime and as an identification/verification of goods technique.

It will be observed that the present invention has apparent utility in a wide variety of fields beyond those described herein. The disclosure herein illustrates the presently-known preferred embodiments for utilizing the labeling technique of the present invention. It will be readily apparent to those skilled in the art that a wide variety of other objects may be suitably labeled in accordance with the precepts of the present invention for their identification and/or verification. Such additional objects and circumstances are included within the scope of the present invention in accordance with the precepts thereof. All citations referred to herein are incorporated expressly herein by reference.

I claim:

1. Method for labeling an object for identification which comprises the steps of:
    (a) applying a first mark comprising a hologram to said object which mark is visible to the naked eye; and
    (b) applying a second mark to said object which mark is invisible to the naked eye, said second mark being one or more of an ultraviolet radiation (UV) dye which is visible to the naked eye only in the presence of ultraviolet radiation, an infrared (IR) dye which is visible to the naked eye only in the presence of infrared radiation, an ink which displays a measurable electrical resistivity or magnetic property, or a biologic marker.

2. The method of claim 1 wherein said first mark is a hologram which is overprinted with an ink which contains one or more of a UV dye, an IR dye, or a biologic marker.

3. The method of claim 1 wherein two or more second marks are applied to said object.

4. The method of claim 3 wherein said second marks comprise a UV dye and a biologic marker.

5. The method of claim 1 wherein said a fluid housed in a pen creates said second mark.

6. The method of claim 4 wherein said ink is housed in a pen.

7. Method for labeling an object for identification which comprises the steps of:
    (a) applying a hologram first mark to said object which hologram mark is visible to the naked eye; and
    (b) overprinting said hologram first mark with a second mark which invisible to the naked eye and which comprises an ink which contains two or more of an ultraviolet (UV) dye which is visible to the naked eye only in the presence of UV radiation, an infrared (IR) dye which is visible to the naked eye only in the presence of IR radiation, or a biologic marker.

8. The method of claim 7 wherein said overprinting of said second mark is created from an ink housed in a pen.

9. The method of claim 7 wherein said biologic marker is one or more of a protein, amino acid, DNA, polypeptide, hormone, or antibody.

* * * * *